United States Patent [19]

Taylor et al.

[11] 4,062,354
[45] Dec. 13, 1977

[54] INTRACRANIAL PRESSURE TRANSDUCER SYSTEM

[76] Inventors: H. Lyndon Taylor; H. Grady Rylander; James L. Story, all c/o University of Texas at Austin, Dept. of Electrical Engineering ENS 436, Austin, Tex. 78712

[21] Appl. No.: 592,361

[22] Filed: July 1, 1975

[51] Int. Cl.² ............................................. A61B 5/00
[52] U.S. Cl. .................................... 128/2 R; 73/410; 128/2 P; 128/2.1 A
[58] Field of Search .................... 128/2 P, 2.1 A, 2 R, 128/2.05 E; 73/410

[56] References Cited

U.S. PATENT DOCUMENTS

| | | | |
|---|---|---|---|
| 3,034,356 | 5/1962 | Bieganski et al. | 128/2 P X |
| 3,340,866 | 9/1967 | Noller | 128/2 P |
| 3,958,558 | 5/1976 | Dunphy et al. | 128/2 P |
| 4,014,319 | 3/1977 | Favre | 128/2 R |

FOREIGN PATENT DOCUMENTS 1,310,439  3/1973  United Kingdom .............. 128/2 P

OTHER PUBLICATIONS

Atkinson, J. R. et al., *Journal of Neurosurgery*, vol. 28, No. 5, 1967, pp. 428–432.
Timm, G. W. et al., *IEEE Trans. on Biomed. Engng.*, May, 1975, pp. 250–251.

*Primary Examiner*—Kyle L. Howell
*Attorney, Agent, or Firm*—Carl B. Fox, Jr.

[57] ABSTRACT

Intracranial pressure transducer System, wherein a holding bracket containing and supporting sensor elements of the apparatus is surgically positioned, through an opening in the skull, against the dura of a neurosurgical patient. The elements within the holding bracket transmit signals in the form of radiated electromagnetic waves to a receiver located outside the body of the patient. The received signals may be recorded on magnetic tape, may be converted to audible sounds, and/or may be recorded on charts, or otherwise suitably preserved and/or presented for use in monitoring the intracranial pressure of the patient.

18 Claims, 6 Drawing Figures

INTRACRANIAL PRESSURE TRANSDUCER SYSTEM

BACKGROUND OF THE INVENTION

Intracranial pressure, that is, pressure within the cranial vault, is an important physical parameter to monitor in patients with intracranial hypertension because intracranial hypertension can often be controlled mechanically and pharmacologically. Physical signs and symptoms of intracranial hypertension are often difficult to interpret and can be misleading. Continuous measurement of intracranial pressure, that is, pressure within the cranial vault, provides the most reliable data base to guide the management of intracranial hypertension in a wide spectrum of neurosurgical patients.

"Intracranial pressure" has traditionally meant "intraventricular fluid pressure". The term "intracranial pressure" has become ambiguous in the last decades since different intracranial pressures have been measured in the ventricles, the subarachnoid space, the epidural space, and in the brain substance itself. The measurement of intracranial pressure in the epidural space is particularly appealing because of the non-invasive nature of the measurement. However, the epidural pressure (EDP) measurements must be highly correlated with the actual intraventricular fluid pressure before an epidural pressure measurement can be substituted for the more clinically useful intraventricular fluid pressure.

A number of sensor devices reported have presented one or more features of sensitivity, range, stability, and convenience, but none thus far has presented so many of the desired features within a single sensor system. This disclosed induction-powered-oscillator transducer system provides a high correlation between EDP measurements and IVP measurements. It further provides appropriate sensitivity and range for many applications, a slow rate of time change, and a stable mechanical structure which minimizes tissue reaction.

SUMMARY OF THE INVENTION

The intracranial pressure transducer system afforded by the invention provides an inductively powered sensing and transmitting unit which is completely implantable with no wires or tubes penetrating the skin. A receiver unit outside the body receives signals from the implanted unit in the form of radiated electromagnetic waves, and converts the received signals to a suitable form for use. The received signals may be recorded, displayed, or heard, or all of these manifestations of the signals may be produced simultaneously. A holding bracket is surgically placed in the skull and against the dura of the patient. The holding bracket then accepts a transducer with a flexible bellows, one end of which is hermetically sealed and the other end of which is closed and positioned against the dura. The flexible bellows supports a ferrite slug from the inside of its closed end. The coil of a high frequency oscillator surrounds the ferrite slug, and when displacement of the bellows occurs as a result of change of epidural pressure, the inductance of the oscillator coil is changed, changing the frequency of the oscillator. These frequencies are electromagnetically transmitted to be picked up by the receiver. The receiver then converts the information to useful form to be preserved and/or interpreted.

A principal object of the invention is to provide improved apparatus for measuring epidural pressure. Another object of the invention is to provide such apparatus which may be used to measure epidural pressure over long periods of time. Still another object of the invention is to provide such apparatus which is accurate, dependable, safe and economical. Another object of the invention is to provide such apparatus which provides measurements of epidural pressure which may reliably be related to intraventricular pressure. A further object of the invention is to provide such apparatus for measuring epidural intracranial pressure which utilizes inductive energy from an external system to power a sensing module, and which provides means for receiving and displaying the received signal. Another object of the invention is to provide such a system wherein a holding bracket is affixed rigidly to the skull, and wherein the holding bracket accepts the transducing portion of the apparatus. Another object of the invention is to provide such a system wherein the apparatus is not subject to pressure drift over lengthy periods of time and is not subject to measurement variations resulting from changes in temperature.

Other objects and advantages of the invention will appear from the following detailed description of a preferred embodiment thereof, reference being made to the accompanying drawings.

DESCRIPTION OF THE PREFERRED EMBODIMENT

Figure 1:
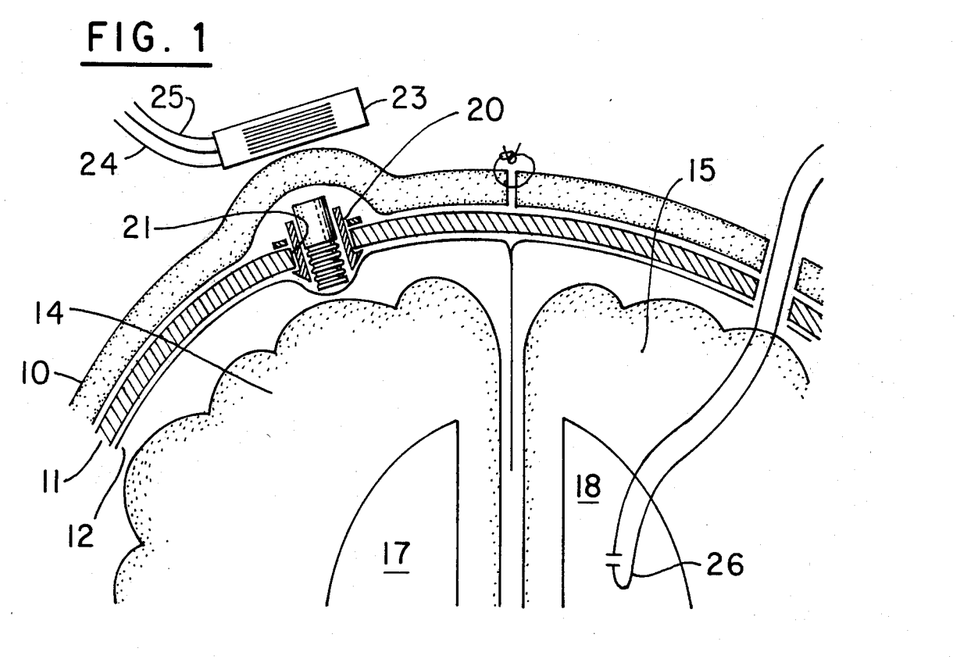
FIG. 1 is a schematic cross-sectional view showing a preferred embodiment of apparatus according to the invention in position for use, and also illustrating schematically an apparatus for direct measurement of intraventricular pressure.

Referring to the drawings in detail, and first to FIG. 1, there are illustrated the scalp 10, skull 11, and dura 12 of a person within which are disposed the right and left cortexes 14 and 15 and the left and right ventricles 17, 18. These elements of the human body are not fully and accurately shown, and are presented in FIG. 1 to illustrate their relative positions.

Sensor device 20 is positioned through a hole 21 through the skull 11. The scalp 10 covers the outer side of sensor 20, the scalp having been incised and sewn back together after implantation of sensor 20. The inner side of the sensor 20 is disposed against the dura 12, causing an inward bulge in the dura. Scalp 10 bulges slightly outwardly at the location of the sensor. An antenna coil device 23 is positioned outside of the scalp adjacent the sensor 20, and is connected by two transmission lines 25 and 24 to apparatus for sending the power signal and receiving for recording and/or audibly and/or visually presenting the received information.

Element 26 is a schematic representation of a device for directly measuring intraventricular fluid pressure.

Figure 2:
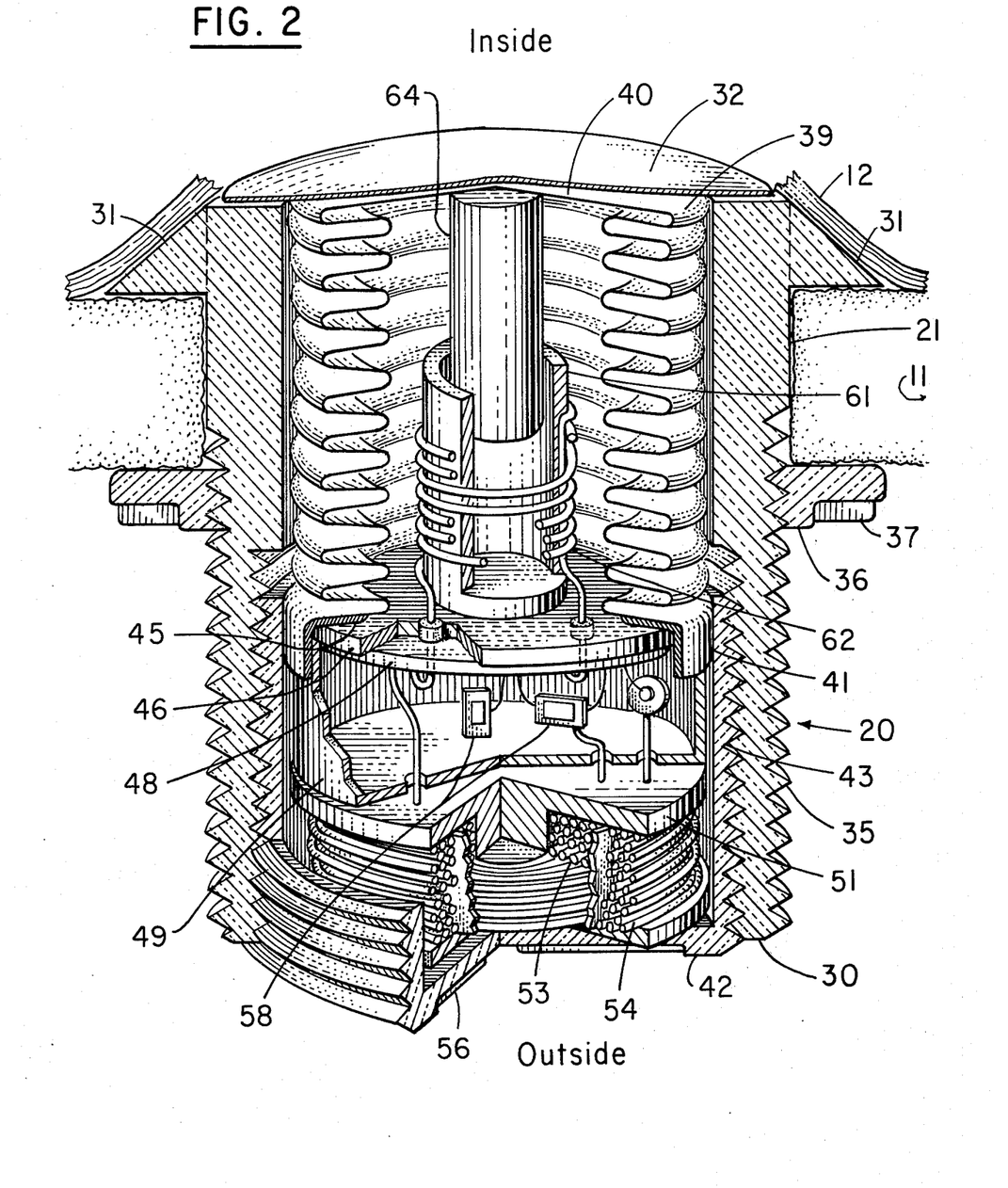
FIG. 2 is an enlarged perspective view, in cross-section, of the implanted signal transmitter element shown in FIG. 1.

Sensor 20 is illustrated in greater detail in FIG. 2. The inner end of sensor 20, as shown in FIG. 1, is shown at the top of FIG. 2, and the outer end of sensor 20 is shown at the bottom of FIG. 2.

Holding bracket 30 of the implanted apparatus is in the form of a tubular sleeve, and has at its inner end two or more outwardly extending lugs 31 of triangular cross-section, as shown in FIG. 2, the outer faces of which are disposed against the inner-table of the skull. Bracket 30 is inserted through opening 21 which has side enlargements (not shown) as necessary to permit passage of the lugs 31. The holding bracket is rotated after insertion to bring the lugs against the inner-table of the skull. The inner end of tubular bracket 30 is covered and sealed by a flexible membrane 32, which is sealed around the entire end of tubular bracket 30. Membrane 32, formed of an inert and impervious material such as fluoropolymers, prevents movement of body fluids into bracket 30, thereby preventing formation of incrustations and like formations and entry of debris which would interfere with the operation of the apparatus. In addition, membrane 32 provides an inert membrane between the transducer bellows and the dura which prevents or minimizes tissue reaction against the device.

The dura 12, more fully called the dura-mater, is the outermost and toughest of the membranes covering the brain, and is disposed flushly against the inner side of membrane 32. The implantation of bracket 30 must, of course, be performed surgically under controlled surgical conditions, in order to achieve effective operation of the herein disclosed apparatus. The lugs 31 serve to control the degree of insertion of the sensor and the displacement of the dura 12, thereby controlling the pressure of the dura against the membrane 32 and making the operation of the apparatus as implanted in the skulls of different patients substantially uniform.

Tubular bracket 30 is externally threaded at 35, the threads extending from the outer end of bracket 30 to the outer-table of the skull 11. An internally threaded ring 36 is screwed onto threads 35 and tightened against the outer-table of the skull, the skull thereby being clamped between lugs 31 and ring 36. Ring 36 has formations 37 to enable tightening of the ring when it is screwed against the outer-table of the skull.

Membrane 32 is flexible in order that it can move in response to changes in epidural pressure. A flexible bellows 39 is disposed with its sealed end 40 against membrane 32. The outer end of bellows 39 is clamped at 41 against the inner surface of an outwardly threaded sleeve 42 screwed into interior threads 43 of the tubular bracket 30.

A ferromagnetic steel plate or platform 46 is hermetically sealed against the inturned flange portion of the bellows at 45 by means of solder or other bonding material. This arrangement forms a hermetic seal around the inner end of the bellows. A ceramic thin-film microcircuit 48 is carried on platform 46 and carries circuitry utilized in the invention.

A ferromagnetic steel cap 49 in the form of a cup is telescopically engaged within the flange of the bellows at 45, its inner edge being in contact with platform 46 to form a shield around the enclosed electrical components. A polymer coil form 51 is disposed against the outer side of cap 49, and carries the antenna and power coils 54, 53, respectively. Sleeve 42, which is closed at its outer end to form a cap, has radial rib formations 56 to enable tightening when the transducer is screwed into threads 43. Discrete electrical components 58 of the electrical circuit are disposed within the space within ferromagnetic cap 49. A polymer coil form 61 is supported within bellows 39 by platform 46. Coil form 61 supports transducing coil 62. A ferrite cylinder or slug 64 is carried at the center of the inner surface of end 40 of bellows 39.

Figure 3:
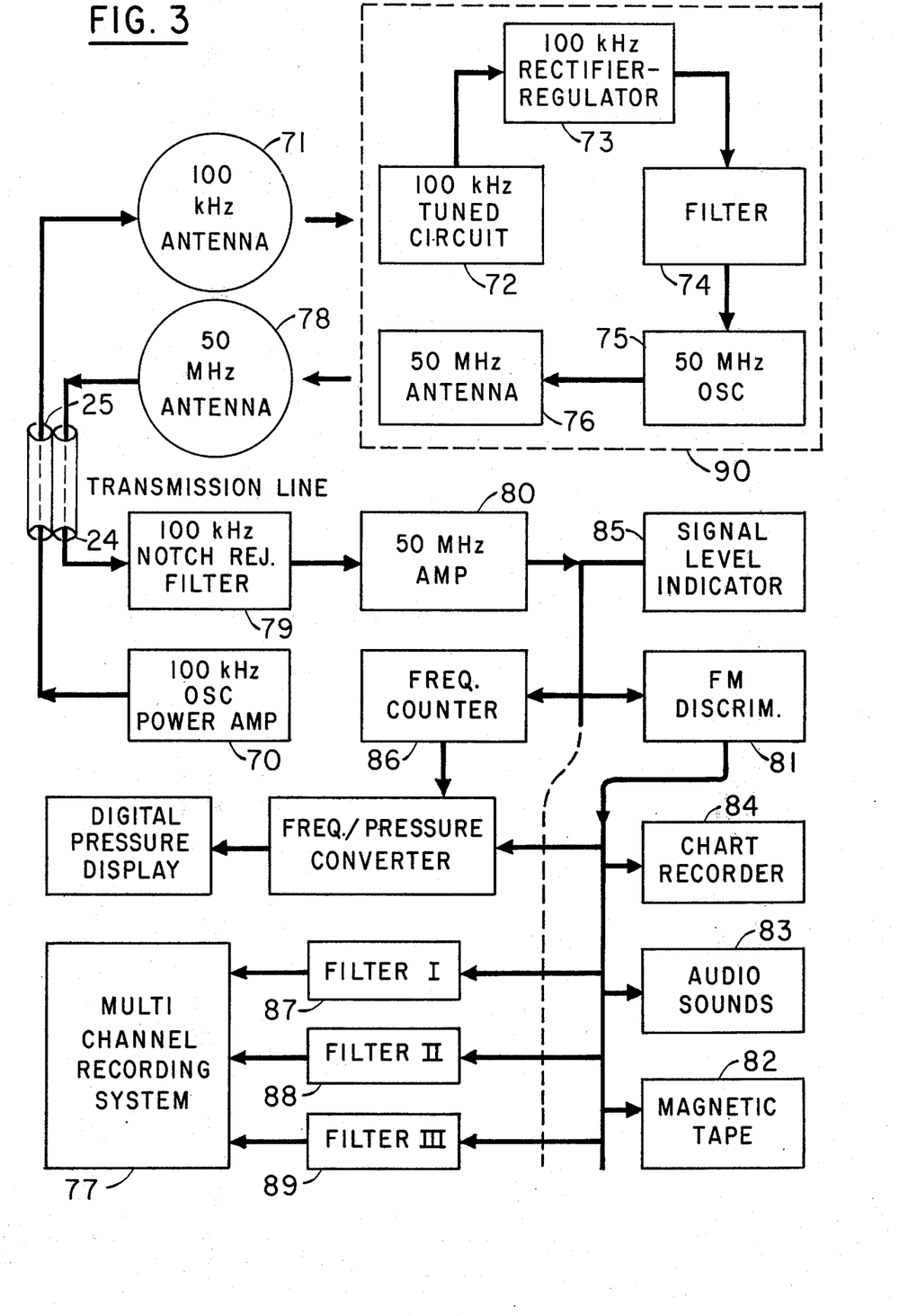
FIG. 3 is a block diagram of the functional components of the transducer and the external monitoring equipment.

Referring now to FIG. 3 of the drawings, a 100 kHz oscillator power amplifier 70 is connected through transmission line 25 to 100 kHz antenna 71. The output of antenna 71 is received by 100 kHz rectifier-regulator 73 and filter 74, thus providing a dc voltage supply for the 50 MHz oscillator 75 to 50 MHz antenna 53.

The output of antenna 53 is received by 50 MHz antenna 78 connected through transmission line 24 to 100 kHz notch rejection filter 79. The signal is then passed through 50 MHz amplifier 80 and possibly conducted to FM discriminator 81, the output from which may be conducted to any or all of a magnetic tape recording device 82, an audio sound production device 83, a chart recorder 84, or selective filters 87, 88, or 89 and an appropriate recording system 77. The dashed line down to the filters suggests direct operations on the carrier signal rather than previously operating on it with an FM discriminator. A signal level indicator 85 is provided to monitor the amplitude of the signal. The signal may be alternatively or simultaneously be applied to a digital frequency counter, a digital-to-digital converter and displayed as a digital pressure numerical value. The continuous signal may be filtered to extract pulse rate and respiratory rate information in addition to the EDP. The elements within dashed line 90 are are contained within tubular bracket 30, the implanted portion of the apparatus. The coils of antenna 71, 78 are contained in element 23 of FIG. 1. The components shown in FIG. 3 outside of dashed line 90 are well known in the art, and may be provided by a person skilled in the art, and further description is not necessary.

Figure 4:
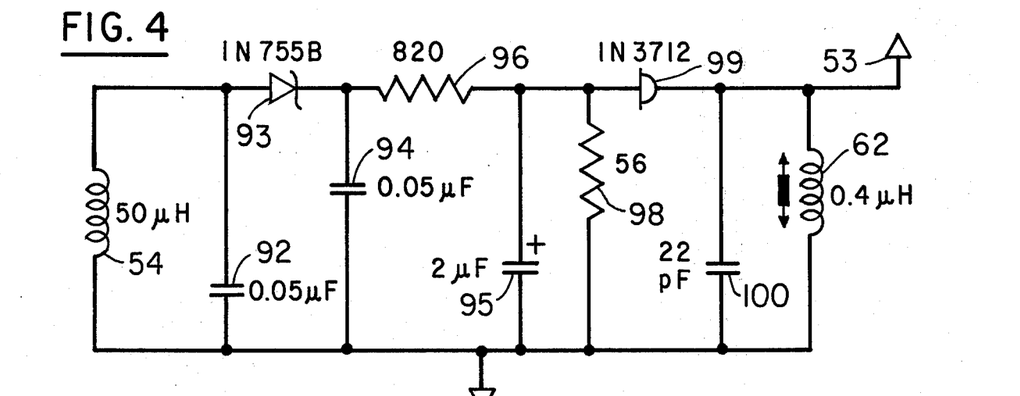
FIG. 4 is a circuit diagram of the sensor portion of the apparatus.

The sensor circuit is shown in FIG. 4. The input inductor 54 (L = 50 $\mu$H [50 microhenries]) in parallel with the capacitor 92 (C = 0.05 $\mu$F [five-hundredths microfared]) exhibits resonance at 100 kHz (or other desired frequency). Exposing this tuned circuit to an external 100 kHz field causes an induced oscillation to be stimulated at the resonant frequency. Sufficient voltage amplitude can be induced in the tuned 100 kHz receiving circuit to permit the regulator diode 93 ("Zener" diode) to serve as both rectifier and regulator in a half-wave rectifier circuit. Full-wave rectification could be used, but would require more components and would occupy a larger space.

The rectified voltage available from the tuned circuit can charge the filter capacitors 94 and 95 to a dc voltage polarity. The 820 ohm resistor combined with the capacitors forms a filter to smooth the rectified (pulsating) ac voltage through the diode 93 into an approximately constant dc potential. The 820 ohms in series with the 56 ohm resistor 98 forms a voltage divider to supply the bias voltage to a tunnel diode oscillator circuit.

The tunnel diode oscillator circuit consists of the properly-biased (approximately 180–200 mV) tunnel diode 99 and the parallel capacitor 100 (22 pF [22 picofarads]) and inductor 62 of approximately 0.4 $\mu$H (four-tenths microhenry) to obtain a frequency near 50 MHz.

The resonant frequency of the LC tank circuit depends on the inductance value L. The inductance of the coil depends on the physical position of ferrite slug 64 disposed relatively moveably along the coil axis. Displacement of the slug changes the frequency of the oscillator. The radiating antenna 53 for the approximately 50 MHz frequency (or other desired frequency) consists of a length of wire coupled by (parasitic) capacitance to the input coil of 50 μH to give a current path for the antenna 53 which radiates the signal generated by the tunnel diode oscillator circuits.

A high Q (quality factor) circuit will oscillate with about 180 mV applied to the tunnel diode. That oscillating frequency near 50 mHz can be radiated a short distance to the pick-up antenna 78. Displacing the ferrite slug 64 by flexing of the end of the Hooke's Law bellows structure 39 makes possible interpretation of a frequency change in terms of a pressure change exerted against the end of the bellows through membrane 32. The frequency change can be calibrated and interpreted as pressure (force/area), force (through Hooke's Law), or displacement in various sensor applications.

Temperature changes of the gas trapped inside the hermetically sealed bellows structure cause those force contributions to change. Hence, the frequency tends to change because temperature changes. To compensate for the effect of the entrapped gas, the temperature coefficient of the capacitor 100 in the tunnel diode oscillator circuit can have an "opposite" temperature effect so that the two effects cancel. For an external compressive force on the bellows 39 causing the movement of the slug 64 to increase the inductance, the capacitor 100 should have a positive temperature coefficient of capacitance (+TCC). If an external compressive force on the bellows 39 causes the movement of the slug 64 to decrease the inductance, the capacitor 100 should have a negative temperature coefficient of capacitance (−TCC). Correct choice of components can cause the net thermal effect to be satisfactorily small.

Any frequency between 20 kHz and 500 kHz would be satisfactory for the induction power supply. Any frequency from about 10 MHz to 200 MHz would be satisfactory for the information-bearing frequency. For clear separation of the two frequencies, the greater the frequency difference between them, the more easily the desired frequency isolation can be obtained.

Figure 5:
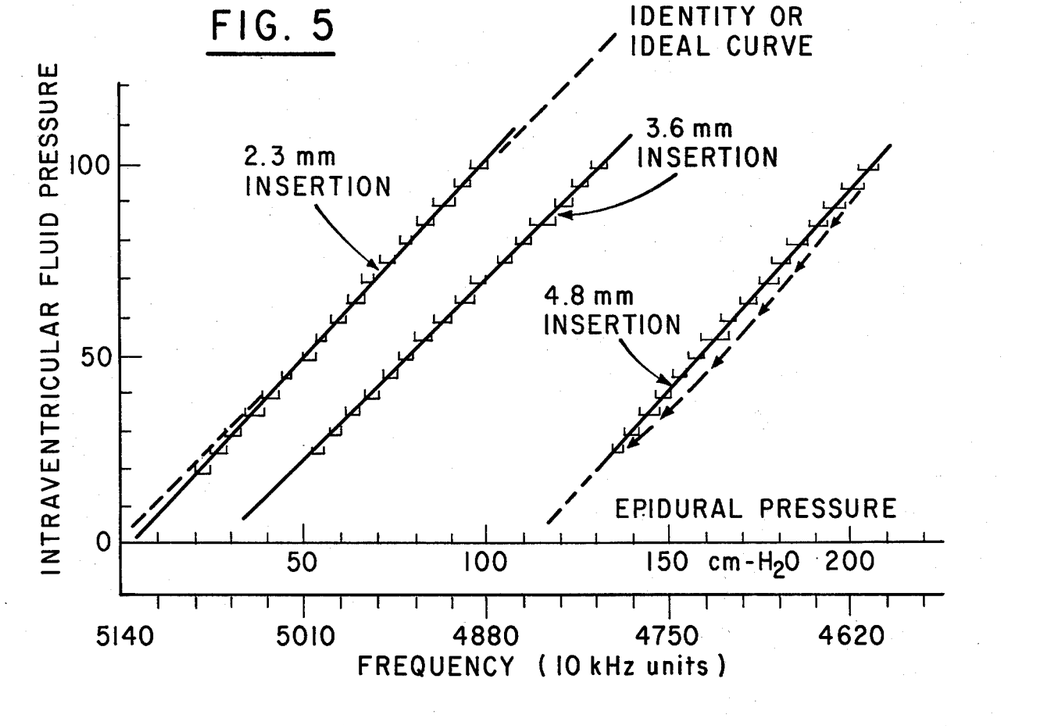
FIG. 5 is a chart illustrating comparative test results achieved according to the invention.

Referring now to FIG. 5 of the drawings, there are shown comparisons between ventricular fluid pressure (IVP) and epidural pressure (EDP) for different depths of insertion of the sensor module beneath the inner table of the skull. The identity or ideal curve is shown as a dashed line at an angle of 45° from the zero point. The EDP curve for 2.3 mm insertion of the sensor follows the identity curve very closely. With increased depth of insertion, curves were produced at 3.6 mm and at 4.8 mm showing higher EDP, but the curves are parallel to the ideal or identity curve so that IVP may be determined at any depth of insertion of the sensor within practical limits. FIG. 5 also shows the frequencies of the signals over the test range.

As will by now be understood, the end of the flexible bellows 39 which supports the ferrite slug 64 is moved as a result of changes of epidural pressure, thereby causing changes in the effective inductance of coil 62. The constant area of the bellows with respect to the dura enables displacement of the bellows and ferrite slug to be used as a measure of change of epidural pressure. The bellows and slug movements are monitored by changes of inductance of coil 62. The hermetically sealed bellows module is stable with time. The bellows and platform 46 are made of metal since the gas permeability of plastic materials precludes their use in fabrication of the sensor element walls. The tubular bracket 30 and associated part are preferably made of a fluoropolymer material such as Teflon. The flexible bellows and membrane may consist of deposited nickel walls and an inert coating which does not introduce creep or hysteresis. Gold and other inert metals, Parylene, and silicon dioxide coatings have shown some degrees of success. In general, the Parylene coatings have been superior to other coatings employed.

Both acute and chronic implantations of the device may be used. IVP and EDP correlation is better in the case of acute implantation than for chronic implantation. As pointed out with regard to FIG. 5, the so-called wedge pressure is greater for deeper implantation than for shallower implantation of the sensor, and becomes approximately zero at implantation in the neighborhood of 2 mm.

Figure 6:
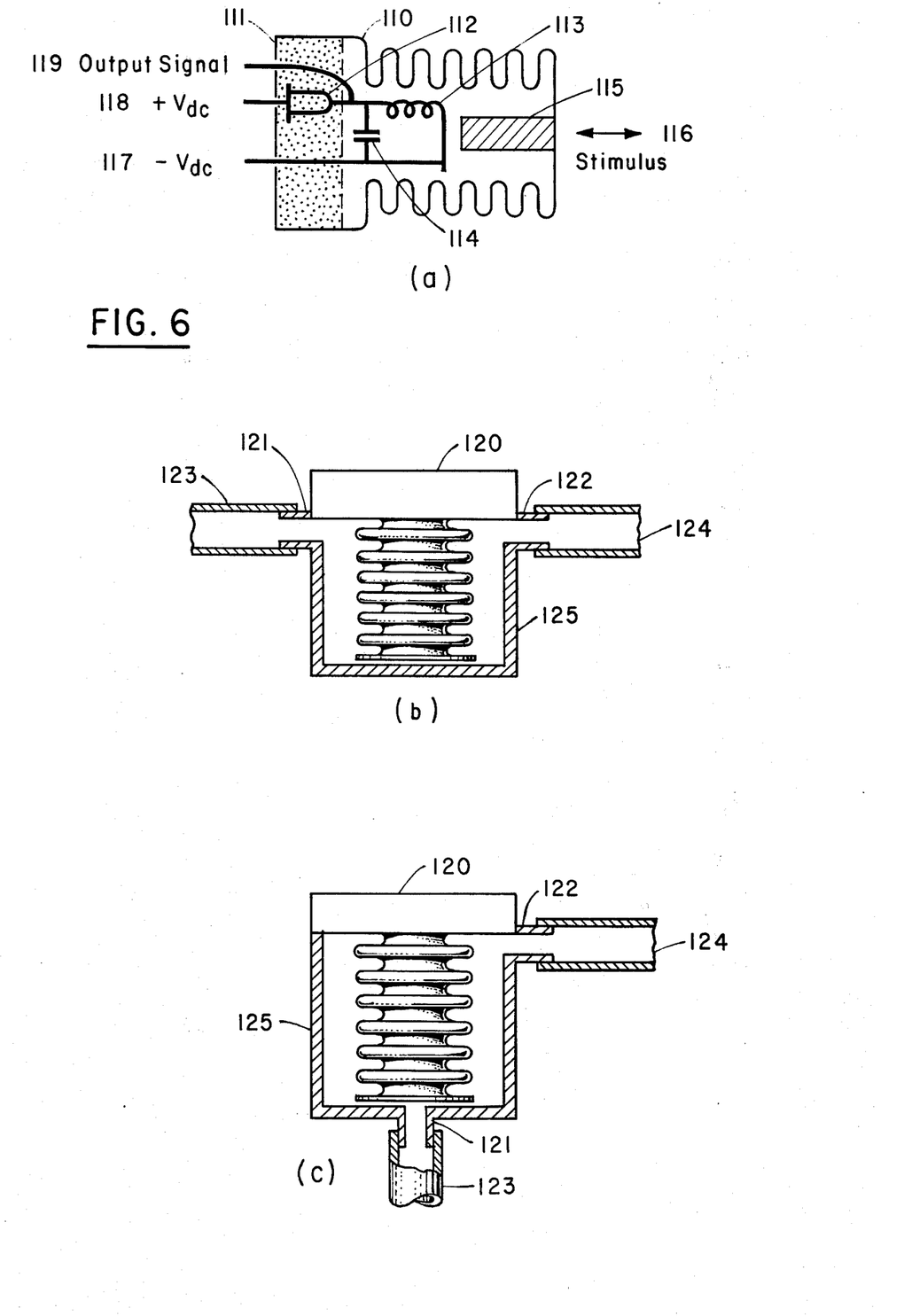
FIG. 6 illustrates modified embodiments which permit combining this pressure sensor with tubing systems as in (b) and (c). Part (a) illustrates the basic elements of the sensor for general use as a displacement, force, or pressure transducer.

Referring now to FIG. 6, selected alternative forms for use of this basic sensor device appear. FIG. 6(a) shows in cross-section a form where signal leads are permissible while using the sensor's capability to give both ac and dc signal information simultaneously for displacement, force, or pressure. The metal bellows 110 with its end seal 111 forms a hermetic container for the sensing circuitry. Mounted within or supported from the end seal 111 are the tunnel diode 112, the coil 113, and the capacitor 114. The ferrite slug 115 must be supported from the opposite end since the differential motion of the two ends of the bellows as caused by a stimulus 116 is that which produces the desired output signal 119. When wires can be permitted connected directly, the voltage can be conducted through a wire for $+V_{dc}$ 118 and a wire for the ground or reference voltage as $-V_{dc}$ 117. Further, the signal can be extracted through a wire at 119.

FIGS. 6(b) and 6(c) illustrate in cross-section a sensor device similar to that of FIG. 2 but housed in an outer shell prepared for coupling into fluid systems consisting of tubes or pipes.

Item 120 represents the sensor device similar to FIG. 2. Item 125 represents the housing to contain the fluid in the vicinity of the bellows of the sensor device 120. Only one port in the housing is necessary but the ports 121 and 122 represent input and output ports to the housing 125. The ports may be nipples to accept tubes such as 123 and 124 in the drawing, or they may be holes to accept tubing or fittings inserted into the port holes (not shown). FIGS. 6(b) and 6(c) illustrate two directional and angular differences for the ports in the housing around the sensor. A wide range of directions, angles, and numbers of ports could all be connected into the housing 125 around the sensor 120. A particular application of concern directly related to epidural intracranial pressure measurement is that of intraventricular measurement of pressure by combining the pressure sensor with a Heyer-Scheulte multipurpose valve and shunt (not shown) and an intraventricular canula 26.

While a preferred embodiment of the invention has been described and shown in the drawings, many modifications thereof may be made by a person skilled in the art without departing from the spirit of the invention, and it is intended to protect by Letters Patent all forms of the invention falling within the scope of the following claims.

We claim:

1. Apparatus for measuring epidural pressure resulting from pressure within the cranial vault of a living person, comprising a tubular holder means having a flexible inert impervious membrane sealed around the terminal end of the tubular wall at one end thereof to close said one end thereof, said one end of said tubular holder means closed by said membrane being adapted for insertion through a hole through the skull to bring said membrane into contact against the dura mater covering of the cranial vault, means for fixedly yet releasably connecting said holder means to the skull, sensing means disposed within said holder means having a portion thereof fixed to said holder means and having a spaced end thereof flushly engaged with said membrane to be movable therewith when said membrane is moved by movement of the dura caused by changes in epidural pressure, transmitter means supported within said holder means for transmitting electromagnetic signals to be received by a receiver outside of said holder means, the frequency of said electromagnetic signals being varied in response to movements of said spaced end of said sensing means engaged with said membrane, and means supported within said holder means for electrically energizing said transmitter means.

2. The combination of claim 30, said sensing means comprising a bellows, said spaced end of said sensing means comprising a closed end of said bellows flushly engaged with said membrane.

3. The combination of claim 2, said means for connecting said holder means to the skull including means for controlling the extent of said one end of said holder means inwardly of the inner surface of the skull.

4. The combination of claim 3, including a ferrite slug disposed within said bellows fixed to said closed end of said bellows; said sensing means including an inductance coil supported within said bellows and disposed spacedly about said ferrite slug and with respect to which said ferrite slug is moved axially by movements of said end of said bellows flushly engaged with said membrane in response to changes in epidural pressure.

5. The combination of claim 4, said means for electrical energizing said transmitter means including an inductively energizable resonant circuit tuned to one frequency disposed within said holder means and adapted to be energized by means disposed outside of said holder means for transmitting electromagnetic signals at said one frequency to said resonant circuit; a series circuit connected to said resonant circuit including means for rectifying and regulating and means for filtering and voltage dividing the output from said resonant circuit and for delivering said output to a tunnel diode oscillator circuit including said induction coil; said transmitter means comprising antenna means disposed within said holder means for producing an electromagnetic field at another frequency in response to oscillation of said oscillator circuit and capable of being received by inductance means disposed outside of said holder means to indicate the epidural pressure at said closed end of said bellows.

6. The combination of claim 6, including ferromagnetic conducting shield means for said resonant circuit and said tunnel diode oscillator circuit.

7. The combination of claim 6, said bellows being hermetically sealed and having entrapped gas therein whereby movements of said closed end of said bellows are effected by changes in temperature, said tunnel diode oscillator circuit including capacitance means having a temperature coefficient of capacitance which at least partially cancels the effect on the inductance of said induction coil caused by said movements of said closed end of said bellows effected by changes in temperature, whereby the net temperature effect on the inductance of said induction coil is minimal.

8. The combination of claim 7, wherein the temperature coefficient of capacitance of said compensating capacitance means is positive.

9. The combination of claim 7, wherein the temperature coefficient of capacitance of said compensating capacitance means is negative.

10. The combination of claim 5, said bellows being constructed of metal.

11. The combination of claim 10, said membrane being constructed of an inert plastic material containing polytetrafluoroethylene.

12. The combination of claim 11, said bellows having an inert coating adapted to prevent corrosion thereof whereby measurements of epidural pressure are not affected by corrosion of the bellows.

13. The combination of claim 6, said means for rectifying and regulating the output from said resonant circuit comprising a single voltage regulator diode.

14. The combination of claim 4, said bellows being constructed of metal.

15. The combination of claim 14, said membrane being constructed of an inert plastic material containing polytetrafluoroethylene.

16. The combination of claim 15, said bellows having an inert coating adapted to prevent corrosion thereof whereby measurements of epidural pressure are not affected by corrosion.

17. Sensing device adapted for displacement by force or pressure, comprising a hermetically sealed bellows structure containing an electronic circuit comprising a tunnel diode and a coil and a capacitor to form an oscillator, a ferrite slug fixed to the interior of a movable end of said bellows structure and extending movably within said coil, an enclosed housing having a membrane sealed at its surrounding edge around a terminal open end of said housing and said housing having no portion extending outwardly of said membrane, said bellows structure being disposed within said housing and having a portion spaced from said movable end thereof fixed to said housing and having said movable end thereof flushly engaged against said membrane, a dc voltage source connected to said oscillator including a resonant circuit which is adapted to be energized by an electromagnetic field produced outside of said housing and a rectifier, the frequency of said oscillator being changed by displacement of said movable bellows end to move said ferrite slug to change the position of said ferrite slug within said coil, the oscillator output frequency being capable of being received outside of said housing for interpretation, said oscillator output frequency including long term frequency magnitude variations and short term alternating current frequency variations as the result of displacement of said movable bellows end by force or pressure.

18. Apparatus for sensing the absolute pressure inside of tubes, pipes, or systems in a manner not requiring wires or tubes to couple directly the sensing system and the system being sensed, comprising a hermetically sealed bellows structure containing an electronic circuit comprising a tunnel diode and a coil and a capacitor to form an oscillator, a ferrite slug fixed to the interior of a movable end of said bellows structure and extending movably within said coil, an enclosed housing having a membrane sealed at its surrounding edge around a terminal open end of said housing and said housing having no portion extending outwardly of said membrane, said bellows structure being disposed within said housing and having a portion spaced from said movable end thereof flushly engaged against said membrane, a dc voltage source connected to said oscillator including a resonant circuit which is adapted to be energized by an electromagnetic field produced outside of said housing and a rectifier, the frequency of said oscillator being changed by displacement of said movable bellows end to move said ferrite slug to change the position of said slug within said coil.

* * * * *